US008071785B2

(12) United States Patent
Langstrom et al.

(10) Patent No.: US 8,071,785 B2
(45) Date of Patent: Dec. 6, 2011

(54) SYNTHESIS AND EVALUATION OF $^{18}$F-LABELLED-ALKYL-1-[(1R)-1-PHENYLETHYL]-1H-IMIDAZOLE-5-CARBOXYLATE AS A TRACER FOR THE QUANTIFICATION OF β-11-HYDROXYLASE ENZYME IN THE ADRENAL GLANDS

(75) Inventors: Bengt Langstrom, Uppsala (SE); Farhad Karimi, Mansfield, MA (US); Elisabeth Blom, Uppsala (SE); Maria Erlandsson, Uppsala (SE)

(73) Assignee: GE Healthcare Limited, Amersham (GB)

( * ) Notice: Subject to any disclaimer, the term of this patent is extended or adjusted under 35 U.S.C. 154(b) by 0 days.

(21) Appl. No.: 12/303,290

(22) PCT Filed: Jun. 7, 2007

(86) PCT No.: PCT/IB2007/001528
§ 371 (c)(1),
(2), (4) Date: Jun. 16, 2009

(87) PCT Pub. No.: WO2007/144725
PCT Pub. Date: Dec. 21, 2007

(65) Prior Publication Data
US 2009/0297447 A1 Dec. 3, 2009

Related U.S. Application Data

(60) Provisional application No. 60/812,159, filed on Jun. 9, 2006.

(51) Int. Cl.
C07D 233/00 (2006.01)
(52) U.S. Cl. .................... 548/334.5; 548/333.5
(58) Field of Classification Search ............... 548/333.5, 548/334.5; 514/399
See application file for complete search history.

(56) References Cited

U.S. PATENT DOCUMENTS

| 7,189,859 B2 * | 3/2007 | Zolle et al. | 548/334.5 |
| 7,358,369 B2 * | 4/2008 | Zolle et al. | 548/334.5 |
| 2005/0033060 A1 | 2/2005 | Zolle et al. | |

OTHER PUBLICATIONS

Wadsak, et.al. "Synthesis of [18F]FETO, a novel potential 11-hydroxylase inhibitor" Journal of Labelled Compounds and Radiopharmaceuticals, J. Wiley, Chichester, GB, vol. 45, No. 4, Nov. 30, 2004, pp. 379-388.*
Wadsak, et.al. "[18F]FETO for adrenocortical PET imaging: a pilot study in healthy volunteers" European Journal of Nuclear Medicine and Molecular Imaging, Springer-Verlag, BE, vol. 33, No. 6 Mar. 28, 2006, pp. 669-672.*
Morissette et al. Advanced Drug Delivery Reviews 2004, 56, 275-300.*
Wadsak et al, (Eur. J. Nuc. Med (2006)).*
Wadsak et al, (J. Label Compd Radiopharm. (2003)).*
Mitterhauser et al, (Eur J. Nucl. Med. (2003), 30 (10); 1398-1401).*
Ansel et al. "Pharmaceutical Dosage Forms and Drug Delivery Systems", 5th ed. (1990), Lea & Febiger, Philadelphia; p. 92-99.*
Lepareur et al. (J. Label Compd. Radiopharm. (2004); 47:857-867).*
Patani et al. (Chem. Rev., 1996, 96(8), 3147-3176).*
Wadsak, et.al. "Synthesis of [18F]FETO, a novel potential 11-hydroxylase inhibitor" Journal of Labelled Compounds and Radiopharmaceuticals, J. Wiley, Chichester, GB, vol. 45, No. 4, Nov. 30, 2004, pp. 379-388.
Wadsak, et.al. "[18F]FETO for adrenocortical PET imaging: a pilot study in healthy volunteers" European Journal of Nuclear Medicine and Molecular Imaging, Springer-Verlag, BE, vol. 33, No. 6 Mar. 28, 2006, pp. 669-672.
PCT/IB2007/001528 Int'l Search Report/Written Opinion dated Dec. 2007.

* cited by examiner

*Primary Examiner* — Andrew D Kosar
*Assistant Examiner* — Valerie Rodriguez-Garcia

(57) ABSTRACT

Radioactively labeled derivatives of (R)-3-(1-phenylethyl)-3H-imidazole-4-carboxylic acid esters and one-step methods for preparing these compounds are provided. The radioactively labelled compounds, and pharmaceutical acceptable salts and solvates are useful as radiopharmaceuticals, especially for use in Positron Emission Tomography (PET) for the diagnosis of adrenal cortical masses such as incidentaloma, adenoma, primary and metastatic cortical carcinoma. Associated kits and method for PET studies are also provided.

3 Claims, No Drawings

SYNTHESIS AND EVALUATION OF $^{18}$F-LABELLED-ALKYL-1-[(1R)-1-PHENYLETHYL]-1H-IMIDAZOLE-5-CARBOXYLATE AS A TRACER FOR THE QUANTIFICATION OF β-11-HYDROXYLASE ENZYME IN THE ADRENAL GLANDS

This application is a national stage entry of PCT/IB07/01528, filed on Jun. 7, 2007 which claims priority from provisional application 60/812,159, filed on Jun. 9, 2006.

FIELD OF THE INVENTION

The invention relates to radioactively labeled derivatives of (R)-3-(1-phenylethyl)-3H-imidazole-4-carboxylic acid esters and methods for preparing these compounds. The invention also relates to the use of these radioactively labelled compounds as radiopharmaceuticals for use as in vivo imaging agents. In particular, these compounds bind selectively to adrenocortical tissue facilitating the diagnosis of adrenal cortical masses such as incidentaloma, adenoma, primary and metastatic cortical carcinoma.

BACKGROUND OF THE INVENTION

The present invention relates to a class of substituted (R)-3-(1-phenylethyl)-3H-imidazole-4-carboxylic acid esters which interact selectively with the mitochondrial cytochrome P-450 species in the adrenal cortex (Vanden Bossche, 1984). When labelled with radiohalogen (iodine-123; bromine-76; fluorine-18 and others) these compounds serve as radiotracers for the diagnosis of adrenal cortical masses such as incidentalomas, adenomas, primary and metastatic cortical carcinoma. When labelled with a betaemitting radionuclide (iodine-131; bromine-82), these radiotracers may be used for radionuclide therapy. The main application is for tumour diagnosis (Khan 2003).

In particular, the compounds according to this invention are potent inhibitors of steroid P450, β-hydroxylation and bind with high affinity to adrenocortical membranes. In fact, the compounds in accordance with this invention have been found to vossess an almost 1000-fold selective affinity when compared with known, clinically used inhibitors (metyrapone, ketoconazole). Therefore, when injected intravenously, the labelled derivatives of the present invention accumulate rapidly in the adrenals, reaching radioactivity levels that are diagnostically useful.

The parent compounds metomidate and etomidate (methyl and ethyl ester; MTO and ETO respectively) are clinically used as a short-acting hypnotic drug. When incubated with human adrenocortical tissue slices, it was shown to block the conversion of 11-deoxycortisol to cortisol and of 11-deoxycorticosterone (DOC) to corticosterone and aldosterone (Weber 1993; Engelhardt 1994). Also metomidate (MTO), the methyl ester, is an equally potent inhibitor of steroid 110-hydroxylation. (R)-configuration of the methyl substituent at the chiral C-atom is essential for enzyme inhibition (Vanden Bossche, 1984).

Clinical findings with the radiotracer [O-methyl-$^{11}$C]metomidate have indicated high uptake in lesions of adrenocortical origin, including adenomas, but very low uptake in lesions of non-adrenocortical origin (Bergstrom 1998; 2000). Specific uptake has been reported in multiple metastases in the lung of a primary adrenocortical carcinoma (Mitterhauser 2002). However, the differentiation between benign (e.g., adenoma) and malignant (e.g., carcinoma) is primarily based on the size and shape of the lesion; irregularities in tumour uptake and multiple lesions are an indication of malignancy (Khan 2003).

Although $^{11}$C-metomidate has "ideal" biological characteristics for scintigraphy of the adrenals and tumor derived therefrom, application of the radiopharmaceutical is limited to hospitals with a PET facility. $^{11}$C is a cyclotron product and decays with a half-life of 20 min, therefore, $^{11}$C-metomidate must be synthesized immediately prior to use.

Halogenations, on the other hand, offer sufficient flexibility, time for preparation and shipment. (Iodine-123 $T_{1/2}$=13.2 hours; Br-76 $T_{1/2}$=16 hours).

Enzyme inhibitors, such as metyrapone have been labelled with radioiodine for adrenal scintigraphy, however, these compounds have never been used for clinical diagnosis (Wieland, 1982; Robien & Zolle, 1983). A comparison of the binding affinities ($IC_{50}$-values) of known inhibitors with etomidate clearly demonstrated the higher potency of etomidate and metomidate.

The available radiotracers for imaging the adrenal cortex and adrenal cortex-derived tumors are labelled cholesterol derivatives. These include 6,β[$^{131}$I]-iodomethyl-19-norcholesterol (NP-59) (Basmadjian, 1975) and 6β-[$^{75}$Se]-selenomethyl-1 g-norcholesterol (Scintadren™) (Sakar, 1976). Both NP-59 and Scintadren™ accumulate in the adrenals slowly, within days, requiring long-lived radionuclides as a label (Iodine-131 $T_{1/2}$=8.04 days; Selen-75 $T_{1/2}$=−120 days). Iodine-131 is also emitting beta-radiation, which contributes considerably to the radiation exposure. The diagnostic use of beta-emitters is no longer state of the art.

In view of the drawbacks of above mentioned agents with respect to patient care (high radiation exposure, repeated imaging procedures), the development of radiolabeled derivatives of etomidate and metomidate would greatly improve radionuclide imaging procedures for the detection and follow-up of adrenal disease.

In a previous study of [$^{18}$F]FETO, (the [$^{18}$F]fluoroethyl ester of etomidate, (R)-1-(1-phenylethyl)-1Himidazole-5-carboxylic acid, 20-[$^{18}$F]fluoroethyl ester), an analogue of [$^{11}$C]MTO and [$^{11}$C]ETO was prepared in the following two step procedure: First, [$^{18}$F]fluoride was reacted with 2-bromoethyl triflate using the kyptofix/acetonitrile method to yield 2-bromo-[$^{18}$F]fluoroethane ([$^{18}$F]BFE). In the second step, [$^{18}$F]BFE was reacted with the tetrabutylaimmonium salt of (R)-1-(1-phenylethyl)-1H-imidazole-5-carboxylic acid to yield [$^{18}$F]FETO. The overall synthesis time was about 80 min (Wadsak & Mitterhauser 2003).

It is desirable to develop an improved one-step $^{18}$F fluorination synthetic methodology which would provide a shorter reaction time (which means faster synthesis of $^{18}$F-labelled compound for production, a higher yield by avoiding side reactions, higher reproducibility and can be easily automated.

A compound thus developed can be used as a radiopharmaceutical to diagnose adrenal cortical masses such as incidentaloma, adenoma, primary and metastatic cortical carcinoma, and have further applications in therapy monitoring.

Discussion or citation of a reference herein shall not be construed as an admission that such reference is prior art to the present invention.

SUMMARY OF THE INVENTION

The present invention provides a compound of formula I, and pharmaceutically acceptable salts and solvates thereof

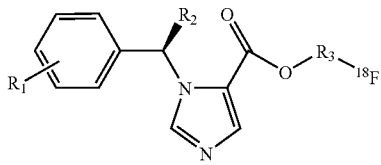

I wherein
R1 is H, Cl, Br, I, F, Me, NO$_2$, or OMe;
R2 is an alkyl group;
R3 is straight or branched alkyl chain containing 1 to 4 carbon atoms.

In a preferred embodiment, compounds of formula I, wherein R1 is a halogen at para-position, R2 is methyl or ethyl group, and R3 contains 1 or 2 carbon atoms, are also provided.

The present invention also provides a method for labeling synthesis, comprising:
(a) providing dry $^{18}$F;
(b) providing a solution of starting material of formula II

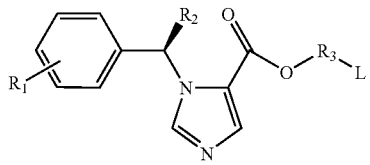

wherein
R1 is H, Cl, Br, I, F, Me, NO$_2$, or OMe;
R2 is an alkyl group;
R3 is straight or branched alkyl chain containing 1 to 4 carbon atoms, and
L is a leaving group;
(c) adding the solution of starting material to dry $^{18}$F and heating the mixture for a predetermined period of time;
(d) collecting the resultant compound of formula I.

In a preferred embodiment, L is TsO, MsO, Cl, or Br.

In yet another embodiment, the invention provides kits for use as PET tracers comprising effective amount of compound of formula I, or pharmaceutically acceptable salts and solvates thereof.

In still another embodiment, the invention provides a method for conducting PET of a subject for in vivo diagnosis or imaging adrenal cortical masses comprising administering to the subject an effective amount of a compound of formula I, or pharmaceutically acceptable salts and solvates thereof, of the instant invention and measuring distribution within the subject of the compound of formula I by PET.

The instant invention also provides a method of monitoring the effect of treatment of a subject with a drug for diseases associated with adrenal cortical masses, said method comprising administering to said subject an effective amount of a compound of formula I, or pharmaceutically acceptable salts and solvates thereof, of the instant invention and detecting the uptake of the compound of formula I by PET.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

One object of the present invention is to provide new synthesis methods and the resultant $^{18}$F-labeled compounds. Such compounds are useful as radio-pharmaceuticals, especially as PET tracers.

Another object of the invention is to provide a novel method for one-step $^{18}$F labeling of biological compound for automated system such as Tracerab®, Fastlab® (both by General Electric Co.) and Synthia® (by Uppsala Imanet, Sweden).

Other advantages using this synthetic methodology are as follows:
1. Shorter reaction time, which means faster synthesis of $^{18}$F-labelled compound for production.
2. Higher yield by avoiding side reaction.
3. Higher reproducibility.
4. Convenient synthetic procedure. Any production chemist can handle the synthesis.
5. The synthesis can be easily automated.
6. Precursors might be easily prepared for marketing.

Efficient $^{18}$F-labeled analogues have special value, since they can be produced in high activity and distributed to other nearby sites for application.

The present invention provides a compound of formula I, and pharmaceutically acceptable salts and solvates thereof

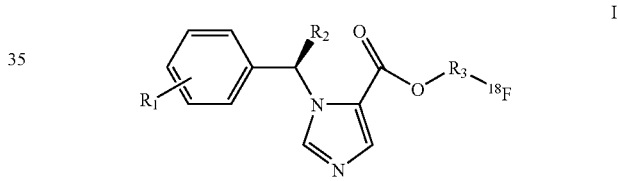

I wherein
R1 is H, Cl, Br, I, F, Me, NO$_2$, or OMe;
R2 is an alkyl group;
R3 is straight or branched alkyl chain containing 1 to 4 carbon atoms.

In a preferred embodiment, compounds of formula I, wherein R1 is a halogen at para-position, R2 is methyl or ethyl group, and R3 contains 1 or 2 carbon atoms, are also provided.

They and their pharmaceutically acceptable salts and/or solvates thereof provide valuable PET tracers in various PET studies. In particular, these compounds bind selectively to adrenocortical tissue facilitating the diagnosis of adrenal cortical masses such as incidentaloma, adenoma, primary and metastatic cortical carcinoma.

In an embodiment of the present invention, it provides kits for use as PET tracers comprising compound of formula I.

It is to be clear that the present invention includes pharmaceutically acceptable salts and solvates of labeled compounds of the instant invention, and mixtures comprising two or more of such labeled compounds, pharmaceutically acceptable salts of the labeled compounds and pharmaceutically acceptable solvates of labeled compounds.

The term "pharmaceutically acceptable" means compatible with the treatment of animals, in particular, humans.

The term "pharmaceutically acceptable salt" refers to salt forms that are pharmacologically suitable for or compatible with the treatment of patients.

If the inventive compound is a base, the desired pharmaceutically acceptable salt may be prepared by an suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cimiamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of the suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "solvate" as used herein means a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The present invention also provides a method for labeling synthesis, comprising:
(e) providing dry $^{18}F$;
(f) providing a solution of starting material of formula II

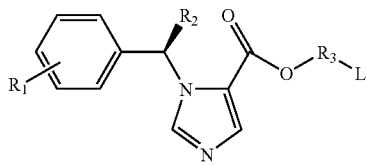

wherein
R1 is H, Cl, Br, I, F, Me, NO$_2$, or OMe;
R2 is an alkyl group;
R3 is straight or branched alkyl chain containing 1 to 4 carbon atoms, and
L is a leaving group;
(g) adding the solution of starting material to dry $^{18}F$ and heating the mixture for a predetermined period of time;
(h) collecting the resultant compound of formula I.
In a preferred embodiment, L is TsO, MsO, Cl, or Br.

General reaction scheme for the synthesis of compound of formula I is a one-step process shown as:

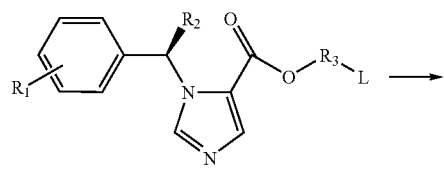

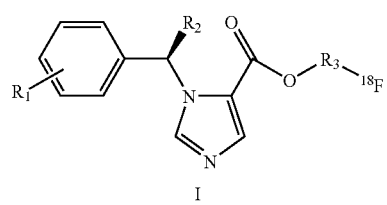

The compound of formula I can be obtained by heating the corresponding starting material together with dry $^{18}F$, followed by LC purification. The overall synthesis time can be in the range of 25 min.

Dry $^{18}F$ can be prepared by the $^{18}O$ (p, n) $^{18}F$ nuclear reaction through proton irradiation of enriched (95%) 180 water using Scanditronix MC-17 cyclotron. After irradiation, the content passes through a pre-conditioned QMA cartridge. The $^{18}F$ adsorbed on the resin is then eluted with acetonitrile-water mixture containing kryptofix and K$_2$CO$_3$. The solution is then evaporated and co-evaporated with anhydrous acetonitrile to dryness in a nitrogen stream at 110° C.

The starting material of the present invention is a compound of formula II:

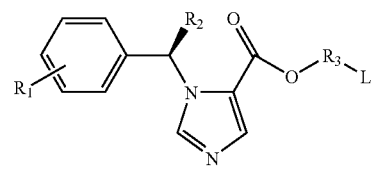

wherein
R1 is H, Cl, Br, I, F, Me, NO$_2$, or OMe;
R2 is an alkyl group such as methyl, ethyl;
R3 is straight or branched alkyl chain containing from 1 to 4 carbon atoms;
L is any leaving group, preferably TsO, MsO, Cl or Br.

In a preferred embodiment, the tosylate derivative may be synthesized from the corresponding alcohol as follows:

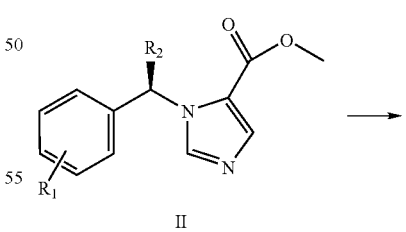

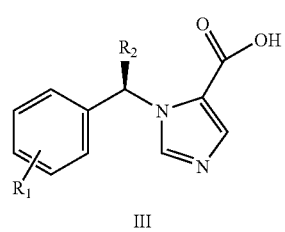

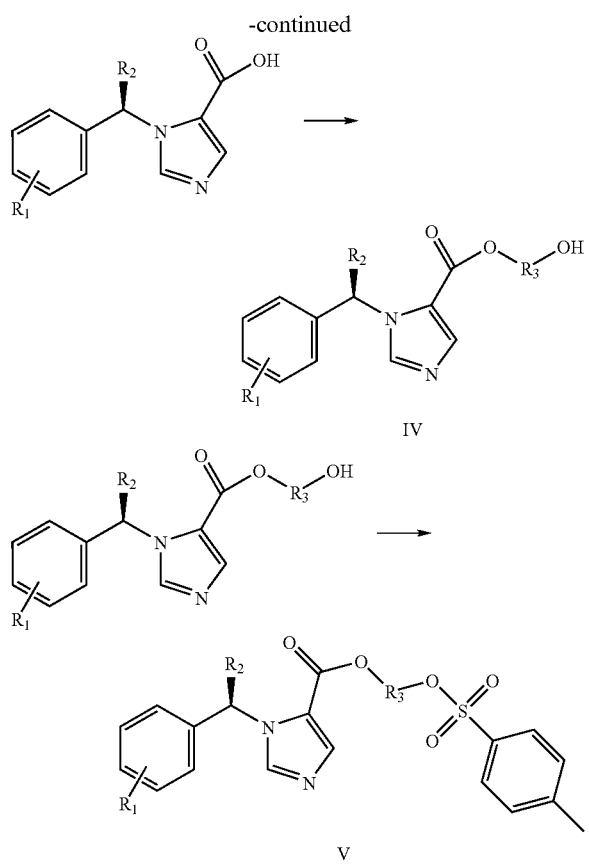

wherein
R1 is H, Cl, Br, I, F, Me, NO$_2$, or OMe;
R2 is an alkyl group such as methyl, ethyl;
R3 is straight or branched alkyl chain containing from 1 to 4 carbon atoms; and
L may be any leaving group such as TsO, MsO, Cl, Br.

The compound (III) and its derivatives might also be synthesized as described in literature (Godefroi et al. 1965). The reaction between compounds III pre-treated with tetrabuthyl ammonium hydroxide and haloalcohol resulted in formation of corresponding alcohol (IV). The compound V can be easily prepared by reaction between p-toluenesulfonyl chloride and IV.

Because of its one-step $^{18}$F fluorination, the synthesis can be easily automated using automated systems, such as TracerLab®, FastLab® or Synthia®. The reaction between the precursor and dry $^{18}$F in anhydrous solvent such as N,N-dimethylformamide can yield the corresponding labeled compound of formula I.

The compounds of formula I, which is $^{18}$F-labelled, or pharmaceutically acceptable salts and solvates thereof, of the invention are suitably formulated into radiopharmaceutical compositions for administration to subjects in a biologically compatible form suitable for administration in vivo. Accordingly, in another aspect, the present invention provides a pharmaceutical composition comprising a radiolabelled compound or pharmaceutically acceptable salts and solvates thereof, of the invention in admixture with a suitable diluent or carrier.

The term an "effective amount" as used herein is that amount sufficient to effect desired results, including clinical results, and, as such, an "effective amount" depends upon the context in which it is being applied.

The term "subject" as used herein includes all members of the animal kingdom including human. The subject is preferably a human.

In preferred embodiment of the present invention, it provides kits for use as PET tracers comprising an effective amount of carbon isotope-labeled ketones, or pharmaceutically acceptable salts and solvates thereof.

Such kits are designed to give sterile products suitable for human administration, e.g. direct injection into the bloodstream. Suitable kits comprise containers (e.g. septum-sealed vials) containing an effective amount of compounds of formula I, or pharmaceutically acceptable salts and solvates thereof.

The kits may optionally further comprise additional components such as radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e., ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The present invention also includes a method for conducting positron emission tomography of a subject for in vivo diagnosis or imaging adrenal cortical masses comprising administering to the subject an effective amount of a compound of formula I, or pharmaceutically acceptable salts and solvates thereof, of the instant invention and measuring the distribution within the subject of the compound by PET. In a preferred embodiment, the invention provides a method for conducting PET of a subject comprising administering to the subject a kit of the instant invention and measuring distribution within the subject of the compound of formula I by PET.

The instant invention also provides a method of monitoring the effect of treatment of a subject with a drug for diseases associated with adrenal cortical masses, said method comprising administering to said subject an effective amount of a compound of formula I, or pharmaceutically acceptable salts and solvates thereof, of the instant invention and detecting the uptake of the compound of formula I by PET.

In accordance with the methods of the invention, the radiolabeled compounds of the invention may be administered to a patient in a variety of forms depending on the selected route of administration, as will be understood by those skilled in the art. The compositions of the invention are preferably administered by intraveneous administration, and the radiopharmaceutical compositions formulated accordingly, for example together with any physiologically and radiologically tolerable vehicle appropriate for administering the compound systemically.

EXAMPLES

The invention is further described in the following examples which are in no way intended to limit the scope of the invention.

Example 1

Reference Synthesis a) Preparation of 2-fluoroethyl 1-[(1R)-1-phenylethyl]-1H-imidazole-5-carboxylate (R)-1-(1-phenylethyl)-1H-imidazole-5-carboxylic acid (200 mg) was dissolved in dichloromethane (2 ml), and then tetrabutyl ammonium hydroxide (TBAH, 40%, 660 mg) was added as a phase transfer catalyst to activate the precursor. The solvent was then evaporated and co-evaporated twice with dichloromethane.

The dried complex was reconstituted in anhydrous DMF (3 ml) and 1-Bromo-2-fluoroethane (200 mg) under argon atmosphere. The reaction mixture was heated at 150° C. for 4.5 h. The excess of 1-Bromo-2-fluoroethane was evaporated under reduced pressure. The residue was extracted with $H_2O$ and dichloromethane, dried with $MgSO_4$ and evaporated under vacuum.

A preparative TLC (eluent: $CH_2Cl_2$/MeOH 9:1) was done to separate the product (9.7 mg, yield 4%). $^1H$- and $^{13}C$-NMR and LC-MS-analysis was performed.

Example 2

Precursor Synthesis a) Preparation of 2-hydroxyethyl 1-[(1R)-1-phenylethyl]-1H-imidazole-5-carboxylate Methyl 1-[(1R)-1-phenylethyl]-1H-imidazole-5-carboxylate was synthesized as described by Godefroi et al. *J. Med. Chem.*, 8, 1965, 220. To a solution of sodium hydroxide (2.64 g) in water (37 ml) were added Methyl 1-[(1R)-1-phenylethyl]-1H-imidazole-5-carboxylate (2.16 g). Upon refluxing for 1 h, at 100° C., the solution was diluted with water (47 ml) and acetic acid (24 ml). The solution was then extracted with $CH_2Cl_2$ and ether, dried with $MgSO_4$ and then concentrated to a small volume, to give the product (1.74 g, 86%). $^1H$- and $^{13}C$-NMR and LC-MS-analysis was performed.

b) Preparation of 2-hydroxyethyl 1-[(1R)-1-phenylethyl]-1H-imidazole-5-carboxylate The precursor was activated by dissolving (R)-1-(1-phenylethyl)-1H-imidazole-5-carboxylic acid (1.740 g) in $CH_2Cl_2$ (2 ml) and adding TBAH (40% in water, 4.64 g). $CH_2Cl_2$ was then evaporated and co-evaporated with $CH_2Cl_2$ two times. The complex was then dried under vacuum.

The dried complex was reconstituted in anhydrous acetonitrile (7 ml) and 2-Iodoethanol (1.65 ml) was added under $N_2$ (g). The solution was evaporated after being stirred for 1 h at 80° C. The mixture was then extracted with $CH_2Cl_2$ and sodiumhydrogen carbonate, dried with $MgSO_4$ and then concentrated to a small volume.

A flash chromatography (eluent: $CH_2Cl_2$/MeOH 9:1) was done on the crude, to separate the title compound (1.7 g). $^1H$-NMR and LC-MS-analysis was performed.

c) Preparation of 2-{[(4-methylphenyl)sulfonyl]oxy}ethyl 1-[(1R)-1-phenylethyl]-1H-imidazole-5-carboxylate To a solution of the 2-hydroxyethyl 1-[(1R)-1-phenylethyl]-1H-imidazole-5-carboxylate (1.73 g) in dry pyridine (13 ml) at 0° C. was added p-toluenesulfonyl chloride (1.7 g) and the mixture was magnetically stirred under $N_{2(g)}$ for 1 h, and further 2 h at r.t. The reaction was followed with TLC, eluent:$CH_2Cl_2$/MeOH, 9:1.

$CH_2Cl_2$ was added and the resulting mixture extracted first with 2M HCl, then by $H_2O$, and then dried with $MgSO_4$. Evaporation of the solvent after filtration, gave a red-yellow crude.

A flash-chromatography (eluent: $CH_2Cl_2$/MeOH 9:1) was done on the crude, to separate the title compound (1.27 g). $^1H$-NMR and LC-MS-analysis was performed.

Example 3

$^{18}F$-labeling Synthesis a) General Method for Preparing $^{18}F$

[$^{18}F$] Fluoride was produced at Uppsala Imanet by the $^{18}O(p, n)$ $^{18}F$ nuclear reaction through proton irradiation of enriched (95%) 18O water using Scanditonix MC-17 cyclotron.

b) Preparation of the [K/K2.2.2]$^{+18}F^-$ (Using Enriched 95% $^{18}O$ Water)

After irradiation, the target content was passed through a pre-conditioned QMA cartridge. The column was purged with helium for five minutes. The [$^{18}F$]fluoride adsorbed on the resin was eluted into a reaction vial with 3 ml of a 96:4 (by volume) acetonitrile-water mixture containing 13.8 mg of kryptofix 2.2.2 and 3.2 mg of $K_2CO_3$; the solution was then evaporated and co-evaporated with anhydrous acetonitrile (2×1 ml) to dryness in a nitrogen stream at 110° C. as shown below.

c) Preparation of the [$^{18}$F] labeled 2-fluoroethyl 1-[(1R)-1-phenylethyl]-1H-imidazole-5-carboxylate using Synthia A solution of 2-{[(4-methylphenyl)sulfonyl]oxy}ethyl 1-[(1R)-1-phenylethyl]-1H-imidazole-5-carboxylate (5.0 mg) in anhydrous DMF (0.5 ml) was added to dry the [K/K2.2.2]$^{+18}$F$^{-}$. The reaction mixture was heated at 150° C. for 15 minutes. The crude mixture was analyzed and purified by High Performance Liquid homotography (HPLC) in an isocratic elution of 50% KH$_2$PO$_4$ (25 mM) and 50% MeCN/H$_2$O (50:7), and a flow rate of 1.5 m/min.

d) Preparation of the [$^{18}$] labeled 2-fluoroethyl 1-[(1R)-1-phenylethyl]-1H-imidazole-5-carboxylate Using Tracerlab A solution of 2-{[(4-methylphenyl)sulfonyl]oxy}ethyl 1-[(1R)-1-phenylethyl]-1H-imidazole-5-carboxylate (4.4 mg) in anhydrous DMF (0.8 ml) was added to dry the [K/K2.2.2]$^{+18}$F$^{-}$. The reaction mixture was heated at 150° C. for 15 minutes. The crude mixture was analyzed and purified by High Performance Liquid homotography (HPLC) in an isocratic elution of 50% KH$_2$PO$_4$ (25 mM) and 50% MeCN/H$_2$O (50:7), and a flow rate of 1.5 ml/min.

SPECIFIC EMBODIMENTS, CITATION OF REFERENCES

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method of making compound of formula I, comprising:
    (a) providing dry $^{18}$F;
    (b) providing a solution of starting material of formula II

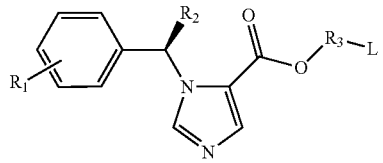

wherein
R$_1$ is H, Cl, Br, I, F, Me, NO$_2$, or OMe;
R$_2$ is an alkyl group;
R$_3$ is a C$_1$-C$_4$ straight or branched alkyl chain, and
L is a leaving group;
    (c) adding the solution of starting material to dry $^{18}$F and heating the mixture for a predetermined period of time; and
    (d) collecting the resultant compound of formula I:

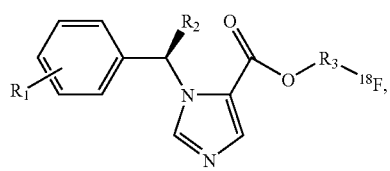

wherein
R$_1$ is H, Cl, Br, I, F, Me, NO$_2$, or OMe;
R$_2$ is an alkyl group;
R$_3$ is a C$_1$-C$_4$ straight or branched alkyl chain, or pharmaceutically acceptable salts thereof.

2. The method of claim 1, wherein R$_1$ is a halogen at the para-position of the aromatic ring, R$_2$ is a methyl or ethyl group, and R$_3$ is a C$_1$-C$_2$ alkyl chain.

3. The method of claim 1, wherein L is TsO, MsO, Cl, or Br.

* * * * *